United States Patent
Allen et al.

(10) Patent No.: US 8,839,724 B2
(45) Date of Patent: Sep. 23, 2014

(54) MODULAR MEDICAL INSTRUMENT TABLE

(75) Inventors: Kraig Herman Allen, Leesburg, IN (US); Gary T. Dane, Bow, NH (US); Jon D. Shoemaker, Leesburg, IN (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 46 days.

(21) Appl. No.: 13/212,613

(22) Filed: Aug. 18, 2011

(65) Prior Publication Data

US 2012/0042808 A1 Feb. 23, 2012

Related U.S. Application Data

(60) Provisional application No. 61/375,494, filed on Aug. 20, 2010.

(51) Int. Cl.
*A47B 57/00* (2006.01)
*A47B 31/00* (2006.01)
*A61B 19/02* (2006.01)

(52) U.S. Cl.
CPC ....... *A61B 19/0248* (2013.01); *A47B 2031/006* (2013.01); *A61B 2019/025* (2013.01); *A61B 2019/0255* (2013.01)
USPC .............. 108/92; 108/103; 108/139; 108/150

(58) Field of Classification Search
USPC ......... 108/94, 92, 93, 95, 103, 145, 139, 150; 312/209
See application file for complete search history.

(56) References Cited

U.S. PATENT DOCUMENTS

| | | | | |
|---|---|---|---|---|
| 1,162,290 A | * | 11/1915 | Koken | 108/94 |
| 3,341,266 A | * | 9/1967 | Schecter et al. | 312/9.46 |
| 3,550,892 A | * | 12/1970 | Propst | 248/282.1 |
| 4,756,429 A | * | 7/1988 | Lehman et al. | 211/43 |
| 4,779,540 A | * | 10/1988 | Dion et al. | 108/98 |
| 4,863,124 A | * | 9/1989 | Ball et al. | 108/28 |
| 4,938,364 A | * | 7/1990 | Stadelman et al. | 211/47 |
| 5,577,344 A | * | 11/1996 | Zaremba et al. | 47/39 |
| 5,704,298 A | * | 1/1998 | Corpuz et al. | 108/50.01 |
| 5,819,960 A | * | 10/1998 | Bonazza | 211/133.1 |
| 5,842,425 A | * | 12/1998 | van der Aa | 108/64 |
| 6,158,360 A | * | 12/2000 | Cheng | 108/103 |
| 6,161,487 A | * | 12/2000 | Chang | 108/50.01 |
| 6,497,184 B1 | * | 12/2002 | Whitesitt | 108/64 |
| 6,568,546 B1 | * | 5/2003 | Huang | 211/205 |
| 6,585,942 B1 | * | 7/2003 | Bussell et al. | 422/300 |
| 6,705,655 B2 | * | 3/2004 | Yang | 294/161 |
| 6,722,511 B1 | * | 4/2004 | Lowe | 211/119.004 |
| 6,877,442 B2 | * | 4/2005 | Helle | 108/147 |
| 6,997,114 B2 | * | 2/2006 | Chang | 108/64 |
| 2008/0087202 A1 | * | 4/2008 | George et al. | 108/50.01 |
| 2009/0015116 A1 | | 1/2009 | Arceta et al. | |
| 2010/0187785 A1 | * | 7/2010 | Knappe et al. | 280/47.34 |

FOREIGN PATENT DOCUMENTS

JP   2009189547 A   8/2009

* cited by examiner

*Primary Examiner* — Daniel Rohrhoff
(74) *Attorney, Agent, or Firm* — Hayes Soloway P.C.

(57) ABSTRACT

A modular medical instrument table and method of using the same is provided. The modular medical instrument table includes a base and at least one support structure rising from the base, the support structure having a substantially vertical axis. At least one arm is removably affixed to the support structure, the arm having a first end proximate to the support structure and a second end distal from the support structure, wherein the second end of the arm is rotatable about the support structure. A shelf is attachable to the second end of the arm.

19 Claims, 9 Drawing Sheets

MODULAR MEDICAL INSTRUMENT TABLE

CROSS REFERENCE TO RELATED APPLICATION

This application claims benefit of U.S. Provisional Application Ser. No. 61/375,494 entitled, "Modular Medical Instrument Table," filed Aug. 20, 2010, the entire disclosure of which is incorporated herein by reference.

FIELD OF THE DISCLOSURE

The present disclosure is generally related to medical holding apparatuses and more particularly is related to a modular medical instrument table and method of making the same.

BACKGROUND OF THE DISCLOSURE

Sterilization trays are used in the medical profession for holding medical instruments. The sterilization trays may be inserted into an autoclave for sterilizing the medical instruments. The sterilization trays may also be used for transporting medical instruments and may be used in various medical settings, such as in an operating room, to retain and organize medical instruments for surgery or other medical application. In these settings, the sterilization trays are exposed to the same contamination hazards as the medical instruments.

When the sterilization trays are used in a medical setting, such as an operating room, they need to be readily accessible to a medical professional. Having the sterilization trays easily accessible allows the medical professional the ability to conduct a quick and proper medical procedure by having convenient access to sterilized medical instruments. Conventionally, sterilization trays may be placed on stationary tables that are out of the way of the working environment of a medical professional. If many medical instruments are needed, then many sterilization trays may be used, which may require a large surface area for the sterilization trays to be placed. Furthermore, sterilization trays that are placed on stationary tables out of the way of the working environment may be less accessible to the medical professional, which in turn, may cause complications within a medical procedure.

Thus, a heretofore unaddressed need exists in the industry to address the aforementioned deficiencies and inadequacies.

SUMMARY OF THE DISCLOSURE

Embodiments of the present disclosure provide a system and method for a modular medical instrument table. Briefly described, in architecture, one embodiment of the system, among others, can be implemented as follows. The modular medical instrument table includes a base and at least one support structure rising from the base, the support structure having a substantially vertical axis. At least one arm is removably affixed to the support structure, the arm having a first end proximate to the support structure and a second end distal from the support structure, wherein the second end of the arm is rotatable about the support structure. A shelf is attachable to the second end of the arm.

The present disclosure can also be viewed as a modular medical instrument table include a movable base and at least two support structures rising from the base, the two support structures each having a substantially vertical axis, wherein the substantially vertical axis of a first of the two support structures is substantially parallel to a substantially vertical axis of a second of the two support structures. At least one arm is removably affixed to each of the support structures, each of the at least one arm has a first end proximate to the support structure and a second end distal from the support structure, wherein the second end of the arm is rotatable about the support structure. At least one extender is positioned in axial alignment with at least one of the two support structures. A shelf is attachable to the second end of the arm, the shelf sized to hold at least one medical instrument container. A rack is positioned on the base, wherein the rack is sized to hold at least one medical instrument container cover.

The present disclosure can also be viewed as providing methods of assembling a modular medical instrument table. In this regard, one embodiment of such a method, among others, can be broadly summarized by the following steps: placing an extender proximate to the arm, wherein the extender is in axial alignment with the support structure; and affixing a second arm to the support structure, wherein the second arm has a first end proximate to the support structure and a second end distal from the support structure, wherein the second end of the second arm is rotatable about the support structure, and wherein the extender is positioned between the arm and the second arm.

The present disclosure can also be viewed as providing methods of using a modular medical instrument table. In this regard, one embodiment of such a method, among others, can be broadly summarized by the following steps: providing a base having at least one support structure rising from the base, the support structure having a substantially vertical axis; placing at least one medical instrument container on a shelf rotatably-attached to an arm, wherein the arm is removably attached to and supported by support structure, wherein the arm has a first end proximate to the support structure and a second end distal from the support structure; and positioning the medical instrument container by rotating the second end of the arm around the support structure.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
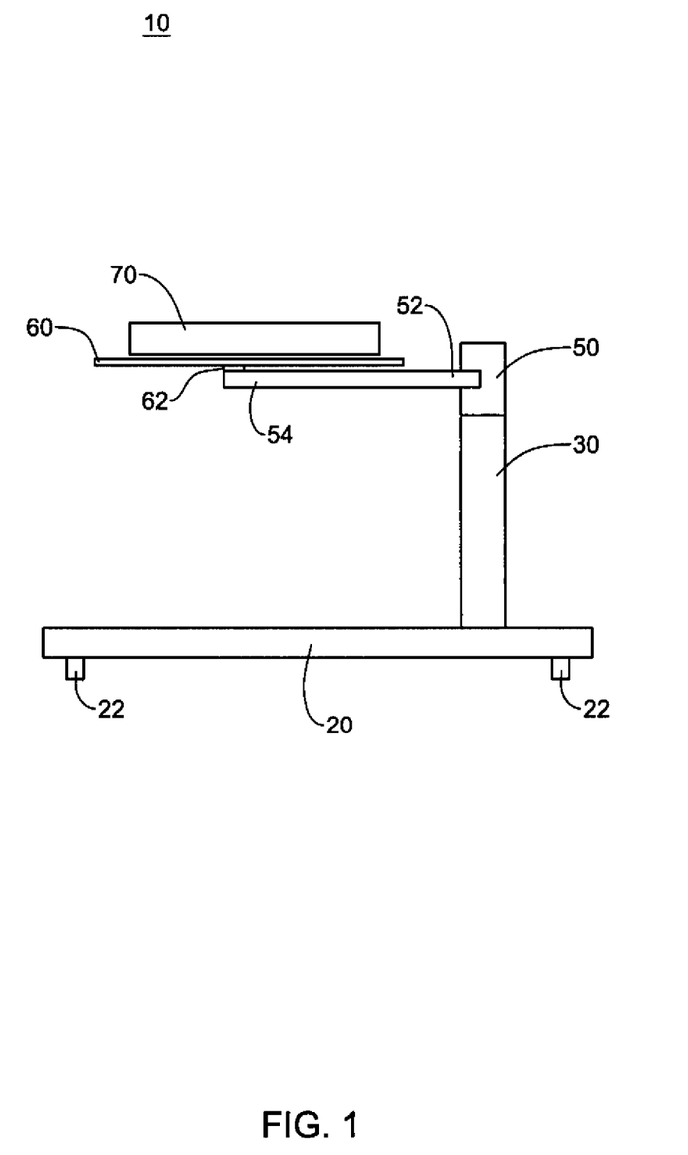
FIG. 1 is a cross-sectional side view illustration of a modular medical instrument table, in accordance with a first exemplary embodiment of the present disclosure.

FIG. 1 is a cross-sectional side view illustration of a modular medical instrument table 10, in accordance with a first exemplary embodiment of the present disclosure. The modular medical instrument table 10, which may be referred to as 'table 10,' includes a base 20, and at least one support structure 30 rising from the base 20, wherein the support structure 30 has a substantially vertical axis. At least one arm 50 is removably affixed to the support structure 30. The arm has a first end 52 proximate to the support structure 30 and a second end 54 distal from the support structure 30. The second end 54 of the arm 50 is rotatable about the support structure 30. A shelf 60 is attachable to the second end 54 of the arm 50.

The table 10 is a modular support for use in a medical operating room or other medical setting. The table 10 may provide simultaneous access to one or multiple medical instrument sterilization containers 70, and allow for efficient access to medical instruments used in medical procedures. The table 10 includes a base 20, which generally resides near a ground surface, such as the floor of an operating room. The base 20 may be placed on the ground, or may be supported by one or more legs 22. The base 20 may be movable, such that it can be positioned in a convenient place where a doctor or other medical professional can easily access it.

At least one support structure 30 is positioned rising from the base 20 such that the support structure has a substantially vertical axis. More than one support structure 30 may be used, as discussed with respect to FIGS. 4-7. The support structure 30 may be affixed to any part of the base 20, such as to a sidewall of the base 20, or along a planar top of the base 20, as is shown in FIG. 1. Additionally, the support structure 30 may be placed in the center of the base 20 or towards an edge of the base 20. In either case, placement of the support structure 30 on the base 20 may be chosen based on efficient use of space, as is discussed further with respect to FIG. 2. The support structure 30 may be permanently affixed to the base 20 or removably affixed to the base 20, and may be constructed from any suitable material, such as stainless steel, plastic, or another material suitable for use in a medical environment. The support structure 30 may have a substantially cylindrical cross-section and an axis that runs along the length of the support structures 30. This axis may be generally parallel to the elongated length of the support structure 30.

Positioned at the top of the support structure 30 is an arm 50, which is removably affixed to the support structure 30. The arm 50 has a first end 52 proximate to the support structure 30 and a second end 54 distal from the support structure 30. The second end 54 of the arm 50 is rotatable about the support structure 30. The arm 50 may be affixed to the support structure 30 by any fastener or design, including a friction fit design where the arm 50 includes a shape that engages with the support structure 30. The connection between the arm 50 and the support structure 30 may allow the arm 50 to rotate with respect to the support structure 30. Specifically, the second end 54 of the arm 50 may rotate around the vertical axis of the support structure 30, which allows the shelf 60 positioned on the second end 54 to be positioned in a variety of locations. This design may allow for convenient access to medical instruments housed within medical instrument containers 70 that are placed on the shelf 60.

The shelf 60 is attachable to the second end 54 of the arm 50, such that the shelf 60 is sufficiently supported by the arm 50. Preferably, the shelf 60 is attached to the second end 54 of the arm 50 with a rotatable attachment device 62 or fastener, such that the shelf 60 is rotatable. For example, the shelf 60 may be rotatable about the point at which the arm 50 supports it, i.e., at the rotatable attachment device 62, as can be seen in FIG. 1. This may allow the shelf 60, and the medical instrument container 70 placed thereon, to rotate in position or about a substantially center point. However, it is also noted that the shelf 60 may be rotatable in other configurations. For example, the shelf 60 may be rotatable about a point that is located on an end or edge of the shelf 60, or in other words, a point that is not substantially in the center of the shelf 60.

It is noted that the table 10 may include at least two different component movements that may be used individually or in combination to provide convenient access to medical instruments. The first movement is the movement of the arm 50 about the support structure 30, which allows the second end 54 of the arm 50 to move around support structure 30, i.e., a rotation of the second end 54 about the elongated axis of the support structure 30. The second movement is the movement of the shelf 60 with respect to the arm 50, wherein the shelf 60 may rotate about a point where it is supported by, i.e., the point of contact between the second end 54 of the arm 50 and the shelf 60. When these two movements are used in combination with one another, a doctor or other medical professional may be able to move the supported medical instrument container 70 in any positioned desired. It is further noted that the table 10 may allow for this movement only when it is manipulated by a user, and not at random times. For example, the arm 50 may be moved when a doctor moves it, but it may stay stationary if a doctor does not manipulate it, regardless of what position it is in.

Figure 2:
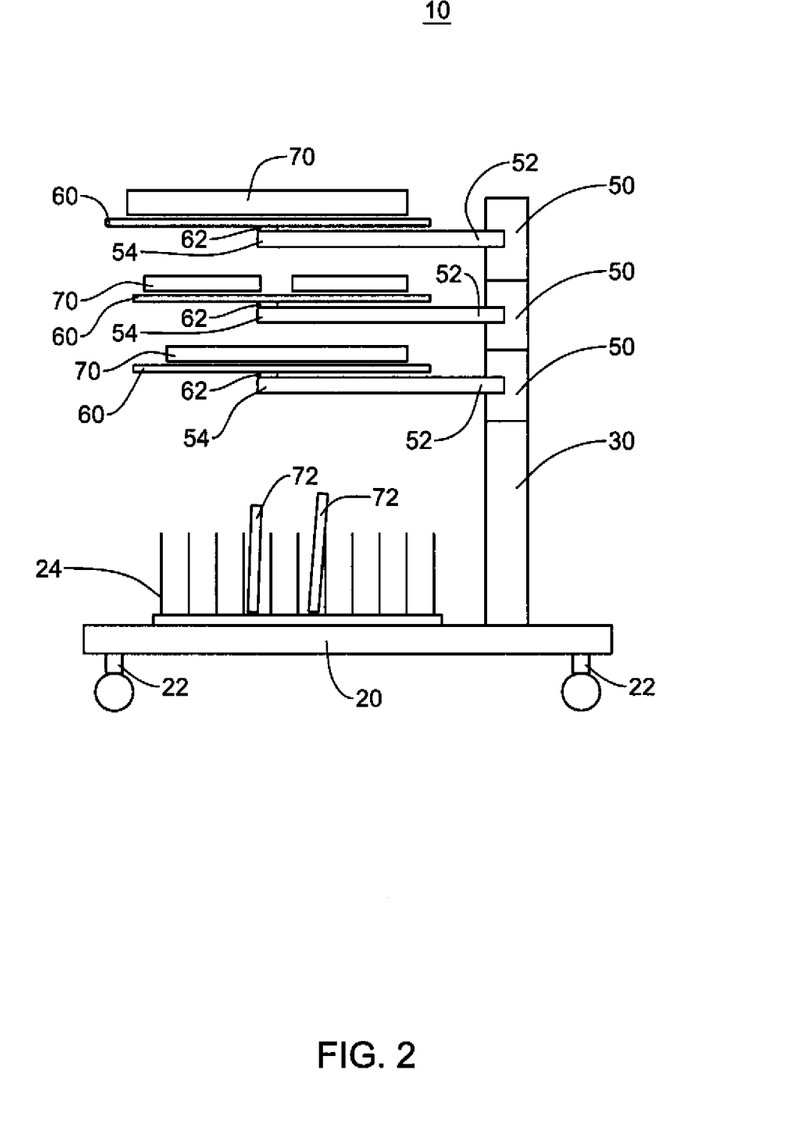
FIG. 2 is a cross-sectional side view illustration of a modular medical instrument table, in accordance with the first exemplary embodiment of the present disclosure.
Figure 6:
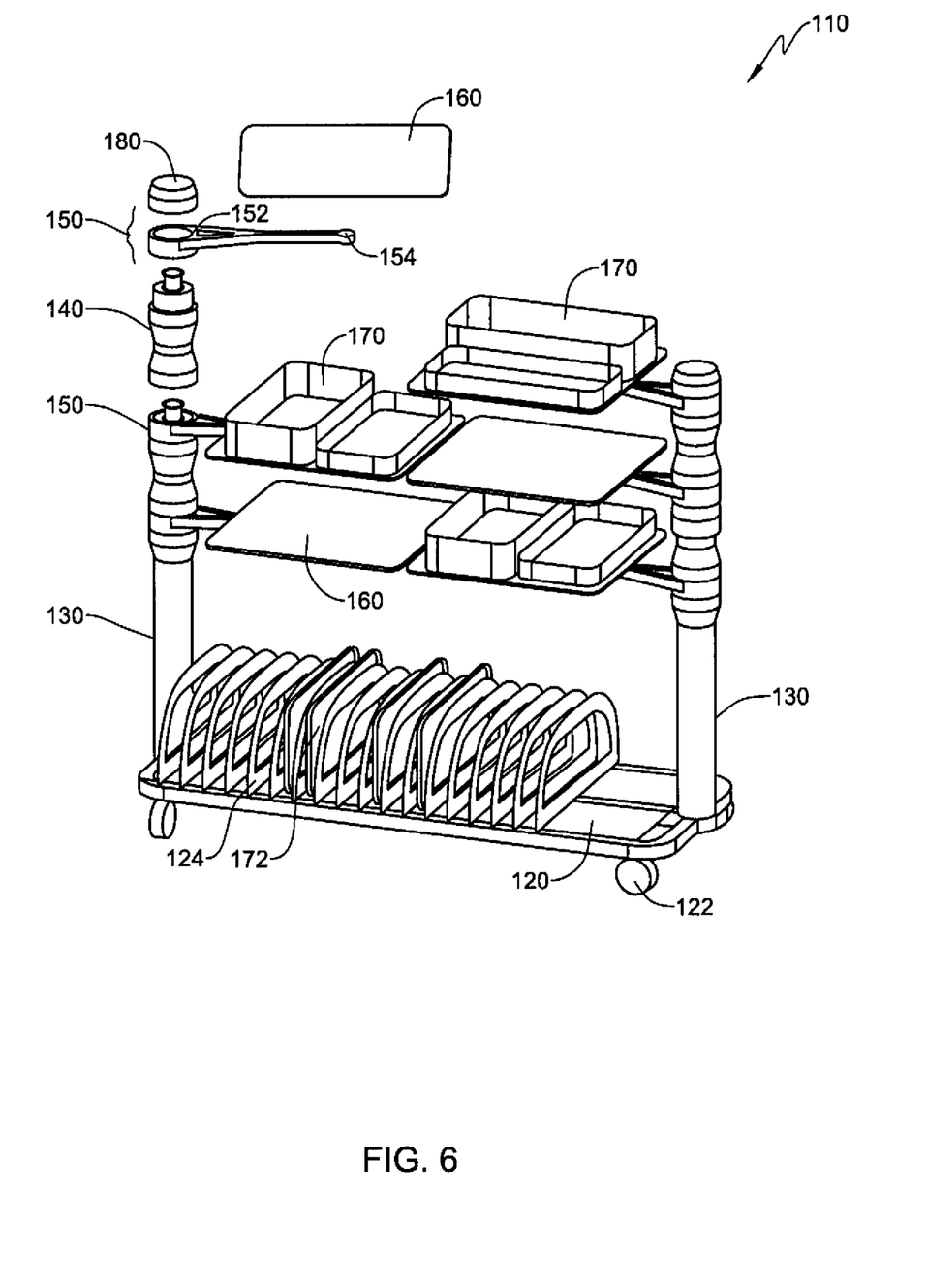
FIG. 6 is a partially exploded plan view illustration of a modular medical instrument table, in accordance with the second exemplary embodiment of the present disclosure.

FIG. 2 is a cross-sectional side view illustration of a modular medical instrument table 10, in accordance with the first exemplary embodiment of the present disclosure. The table 10 of FIG. 2 is substantially similar to the table 10 of FIG. 1, but includes a plurality of arms 50. As can be seen, each of the arms 50 may be attached to the support structure 30 or to another arm 50. This may allow for the stacking of arms 50 that are positioned vertical to one another, so that a plurality of shelves 60 may be used. The arms 50 may each be affixed to either the support structure 30 or another arm 50 with any fastener or design, including a friction fit design where the arm 50 includes a shape that engages with the support structure 30 or another arm 50. The connection between the arm 50 and the support structure 30 or between two arms 50 may allow the arm 50 to rotate with respect to the support structure 30. Specifically, the second end 54 of the arm 50 may rotate around the vertical axis of the support structure 30, which allows the shelf 60 positioned on the second end 54 to be positioned in a variety of locations. When two arms 50 are attached together, one of the two arms 50 may include a connector that engages with the other arm 50. This may be accomplished with a male connectors and female connectors, as is shown in FIG. 6.

The base 20 of the table 10 in FIG. 2 is shown supported by legs 22 with casters, or other movement permitting devices. The casters, which may also be referred to as rollers or wheels, may be lockable to prevent movement, and unlockable to allow movement. Any number of legs 22 with any number or type of casters may be used, all of which are considered within the scope of the present disclosure. The base 20 also includes at least one rack 24, which is used to hold the cover 72 from a medical instrument container 70. The rack 24 may include a plurality of vertical separators that allow for insertion of the covers 72 therebetween. This allows the covers 72 to be stored and kept out of the way when the instruments within the instrument containers are needed. The rack 24 may be one structure, or individual structures that are used to store the covers 72. For example, the rack 24 may include one section on one side of the base 20 and a second section on the other side of the base 20 with the support structure 30 therebetween.

Figure 3:
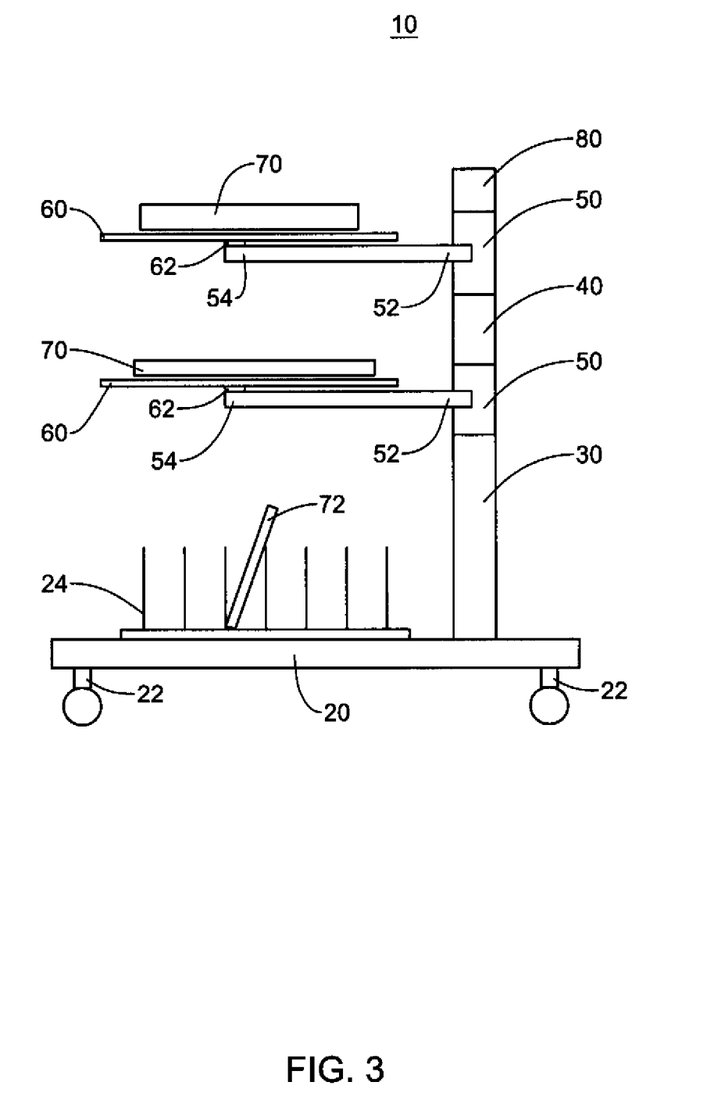
FIG. 3 is a cross-sectional side view illustration of a modular medical instrument table, in accordance with the first exemplary embodiment of the present disclosure.

FIG. 3 is a cross-sectional side view illustration of a modular medical instrument table 10, in accordance with the first exemplary embodiment of the present disclosure. The table 10 includes a plurality of arms 50 which are supported by the support structure 30. An extender 40, which may be considered an extension structure, is positioned between the two arms 50. The extender 40 may be characterized as a structure that spaces two or more arms 50, such that there is a larger distance between two arms 50 than there would be if no extender 40 is used. For example, in FIG. 3, the extender 40 allows for a predetermined distance to be formed between the bottom of the uppermost arm 50 and the top of the medical instrument container 70 on the lowermost shelf 60. This may allow storage of larger medical instruments within the container 70 on the lowermost shelf 60.

Either of the extender 40 or the arms 50 may be immediately affixed to the support structure 30, depending on design. In FIG. 3, one arm 50 is directly attached to the support structure 30 and the extender 40 attached to that arm 50 on a first side. A second arm 50 is attached to the other side of the extender 40. A top cap 80 may be used to cover the uppermost section of the top arm 50. As was described in detail previously, the arms 50 may be removably affixed to the support structure 30 and may rotate about the axis of the support structure 30. In other words, the second end 54 of the arm 50 that supports the shelf 60 may swivel around the support structure 30. The arm 50 may move fully around the support structure 30, or partially around the support structure 30. Furthermore, a locking structure (not shown) may be used to lock the arm 50 in a stationary position in any location about the support structure 30. The same connections and function may be provided when an extender 40 is used, including any of the rotation of components or locking thereof.

At the top of the table 10, a top cap 80 may be primarily used to hold the uppermost arm 50 in place, but may also be used to hold other components in place, such as any of the extenders 40. For example, the top cap 80 may seal off the top of the uppermost arm 50, thereby keeping crevices and other surfaces free from being dirtied or damaged. Within the medical field, sterilization of all components is extremely important to prevent the spread of disease and bacteria. The top cap 80 may seal off the table 10 and thus prevent bacterial from being harbored proximate to the connection structures between the arms 50 and the extender 40.

It is noted that the various components discussed herein could be constructed integral with one another. For example, top cap 80 could be integral with an extender 40 or an arm 50. Likewise, an extender 40 could be built into the arm 50, such that the arm 50 provides the desired distance from another arm 50 when installed on the table 10. Any other configurations which may reduce component costs, manufacturing time, assembly time, or make the use of the table 10 more convenient, more efficient, or better, are considered within the scope of the present disclosure. Additionally, it is noted that the table 10 may include any number of various components. For example, as will be described with respect to FIGS. 4-7 and the second exemplary embodiment, more than one support structure 30 may be used. Each support structure 30 may support any number of arms 50 using any number of extenders 40, wherein each of the arms 50 support any number of shelves 60 which may hold any number of medical instrument containers 70.

In use, the base 20 and support structure 30 may be housed and/or stored in a non-sterile environment, such as the operating suite within a medical facility. The extenders 40, arms 50, shelves 60 and medical instrument containers 70 may be housed in a sterile environment until they are used in a medical procedure. The medical instrument containers 70 may be containers specifically designed to endure a sterilization process, such that they store a sterilized medical instrument during a sterilization process and after a sterilization process. Alternatively, one or more medical instruments may be housed within the medical instrument containers 70 after being sterilized in a separate container or sterilization setting. The medical instruments may include any medical tools, supplies or items used with a medical procedure.

Prior to or during a surgical procedure or other medical procedure, a medical worker may assemble the extenders 40, arms 50, shelves 60 and medical instrument containers 70 in the desired configuration. For example, the medical worker may assemble a table 10 with two support structures 30 to include three arms 50 with two extenders 40, where each of the arms supports a shelf 60. From here, the medical worker may select which medical instrument containers 70 to place on which shelves. The table 10 may be wheeled into place and locked into position once in place with the casters. The medical worker may then rotate the arms 50 and shelves 60 appropriately to allow a doctor or surgeon to access the medical instruments. Once the medical instruments are finished with being used, the various components may be removed from the table 10 and put through a sterilization process within a sterilization apparatus, such as an autoclave. Once sterilized, a single person in the operating room suite, or another location, may assemble the table 10 prior to a subsequent medical procedure.

Figure 4:
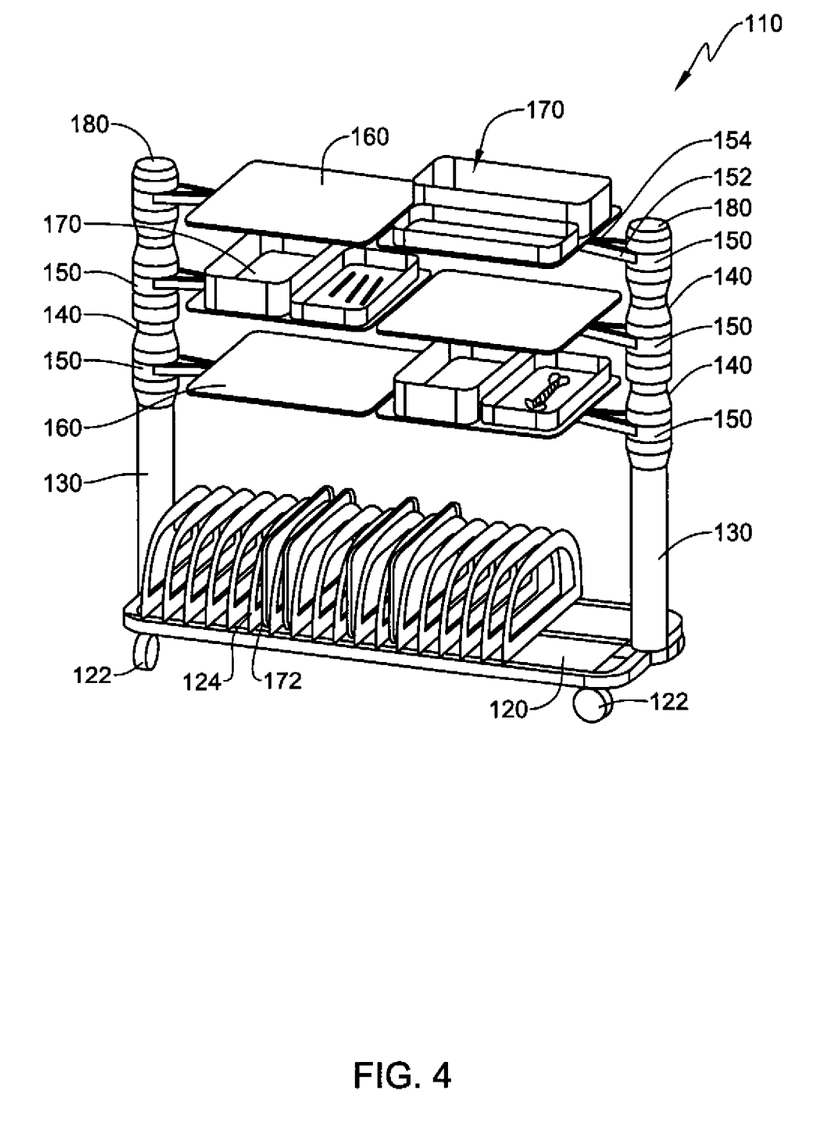
FIG. 4 is a plan view illustration of a modular medical instrument table, in accordance with a second exemplary embodiment of the present disclosure.

FIG. 4 is a plan view illustration of a modular medical instrument table 110, in accordance with a second exemplary embodiment of the present disclosure. The table 110 of the second exemplary embodiment is substantially similar to the table 10 of the first exemplary embodiment, and may include any of the features, components, or functioning described with respect to the first exemplary embodiment. The table 110 includes a base 120, and at least two support structures 130 rising from the base 120, wherein the support structures 130 have a substantially vertical axis. At least one arm 150 is removably affixed to each of the support structures 130. The arms 150 have a first end 152 proximate to the support structure 130 and a second end 154 distal from the support structures 130. The second end 154 of the arms 150 is rotatable about the support structure 130. A plurality of extenders 140 is included between the arms 150, and a top cap 180 is included at the top of the uppermost arm 150. A shelf 160 is attachable to the second end 154 of the arms 150.

The base 120 of the table 110 includes a plurality of locking casters 122 or other movement facilitating devices, such as wheels or rollers. The base 120 is substantially planar and may generally be supported by at least four locking casters 122, however, any number of locking casters 122 may be used. The base 120 includes a rack 124 to hold one or more covers or lids 172 from the medical instrument sterilization containers 170. Two support structures 130 rise substantially vertically from the base 120 and ultimately provide support to at least one medical instrument sterilization container 170. The support structures 130 may be substantially cylindrical and have an axis that runs along the length of the support structures 130.

Either of the extenders 140 or the arm 150 may be immediately affixed to the support structure 130, depending on design. In FIG. 4, an arm 150 is attached to the top of the support structure 130, and an extender 140 is attached to the arm 150. The arm 150 may be removably affixed to the support structure 130, or the extender 140, and may rotate about the axis of the support structure 130. In other words, the second end 154 of the arm 150 that supports the shelf 160 may swivel around the support structure 130. The arm 150 may move fully around the support structure 130, or partially around the support structure 130. Furthermore, a locking structure (not shown) may be used to lock the arm 150 in a stationary position in any location about the support structure 130.

As is shown, a plurality of arms 150 may be used to support a plurality of shelves 160. To provide a gap or distance between the shelves 160, a plurality of extenders 140 may be used to separate the arms 150. The extenders 140 may be removably locked together and may sandwich the arms 150. At the top of the table 110, a top cap 180 may be primarily used to hold the uppermost arm 150 in place, but may also be used to hold other components in place, such as any of the extenders 40. The arms 150 include a first end 152, which is located proximate to the extenders 140, and a second end 154, which is located distal from the extenders 140. Any design of arm 150 may be used, including a "Y" support, as is shown in FIG. 4, where the first end 152 of the arm 150 includes two structures that merge into a signal structure at the distal end 154. The shelves 160 are located at the second end 154 of the arm 150. The shelves 160 may be a substantially planar unit that supports one or more medical instrument sterilization containers 170. The shelves 160 may be dimensioned to interconnect with a medical instrument sterilization container 170. Furthermore, the shelves 160 may be rotatable on the arm structure 150 to maximize accessibility of the medical instrument sterilization containers 170.

In use, the table 120 and support structures 130 may be housed and/or stored in a non-sterile environment, such as the operating suite within a medical facility. The extenders 140, arms 150, shelves 160 and medical instrument sterilization containers 170 may be housed in a sterile environment until they are used in a medical procedure. One or more medical instruments may be housed within the medical instrument sterilization containers 170, along with any other medical tools, supplies or items used with a medical procedure. The extenders 140, arms 150, shelves 160 and medical instrument sterilization containers 170 may be removable from the support structures 130 to allow for a thorough sterilization within a sterilization apparatus, such as an autoclave. From the disassembled state, a single person in the operating room suite, or another location, may assemble the table 110 prior to a medical procedure.

Figure 5:
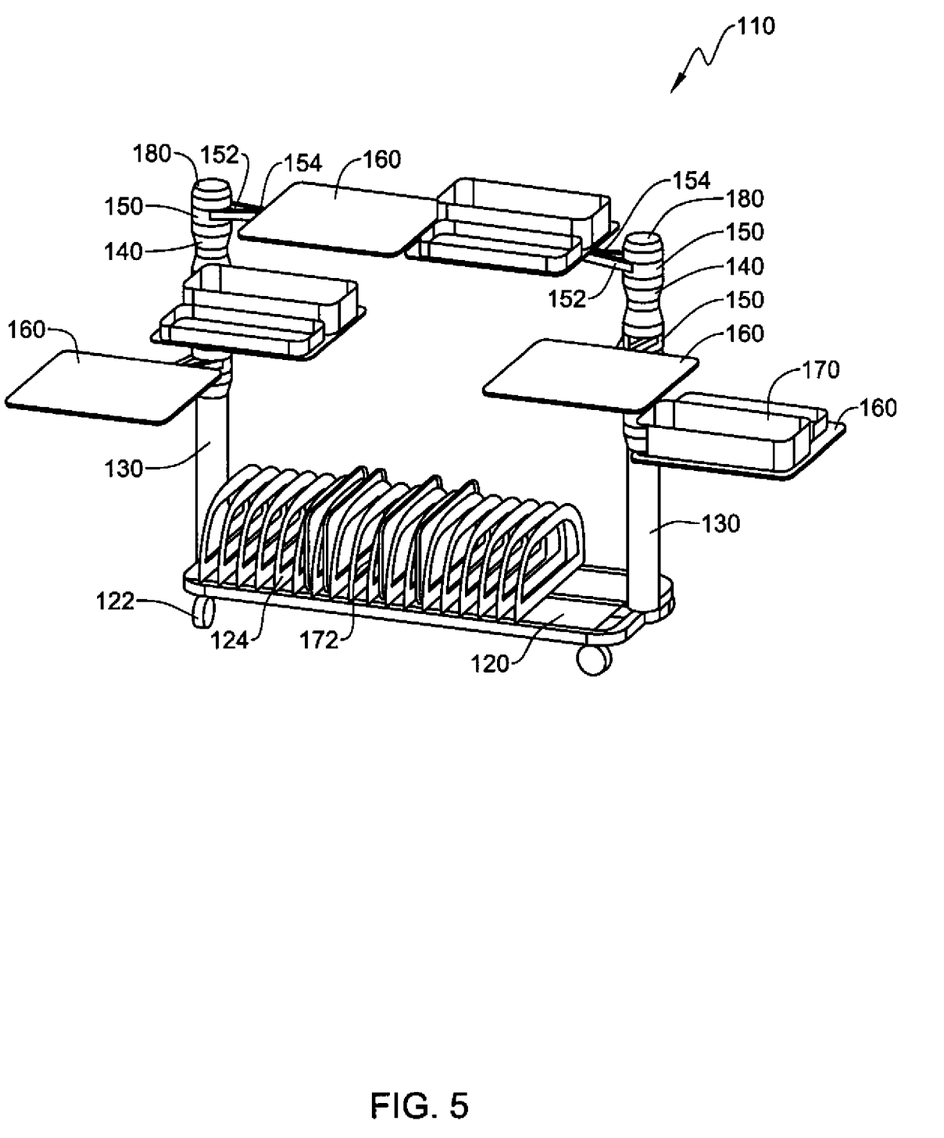
FIG. 5 is a plan view illustration of a modular medical instrument table having arm structures in various positions, in accordance with the second exemplary embodiment of the present disclosure.

FIG. 5 is a plan view illustration of a modular medical instrument table 110 having arms 150 in various positions, in accordance with the second exemplary embodiment of the present disclosure. As can be seen in FIG. 5, the arms 150 may be moved to a variety of positions about the support structures 130. Once in these positions, the arms 150 may be locked in place, or freely movable. This configuration allows the shelves 160 and the medical instrument sterilization containers 170 housed thereon, to be more easily accessible to a medical professional. For example, the arms 150 may be positioned directly above the base 120, as is shown in FIG. 4, prior to a medical procedure. Then, as the medical professional prepares for the medical procedure, the table 110 may be positioned proximate to the operating table, and the arms 150 may be moved in to the appropriate positions to allow convenient and efficient access to medical instruments within the medical instrument sterilization containers 170. A cover 172 from the medical instrument sterilization containers 170 may be removed from the medical instrument sterilization containers 170 and stored on the rack 124 during the medical procedure.

FIG. 6 is a partially exploded plan view illustration of a modular medical instrument table 110, in accordance with the second exemplary embodiment of the present disclosure. As can be seen, the extenders 140, arms 150, shelves 160, medical instrument sterilization containers 170 and top cap 180 may be removable from each other and connected together. The components may be connected together by a variety of connection devices, such as a male and female connection system, as is shown. A user of the table 110 may simply snap the components together to assemble the table 110 for use. After use, the components may be disassembled from each other and sterilized prior to any subsequent use. Other types of connectors may also be used. For example, the support structure 130 may be substantially cylindrical with an outer diameter and the arms 150 and extenders 140 may have a hollow, cylindrical shape, where the interior diameter of the arms 150 and extenders 140 fits over the outer diameter of the support structure 130. This may allow the arms 150 and extenders 140 to simply slide onto the support structures 130. Any other type of connection between the components may be used, and is considered within the scope of the present disclosure.

Figure 7:
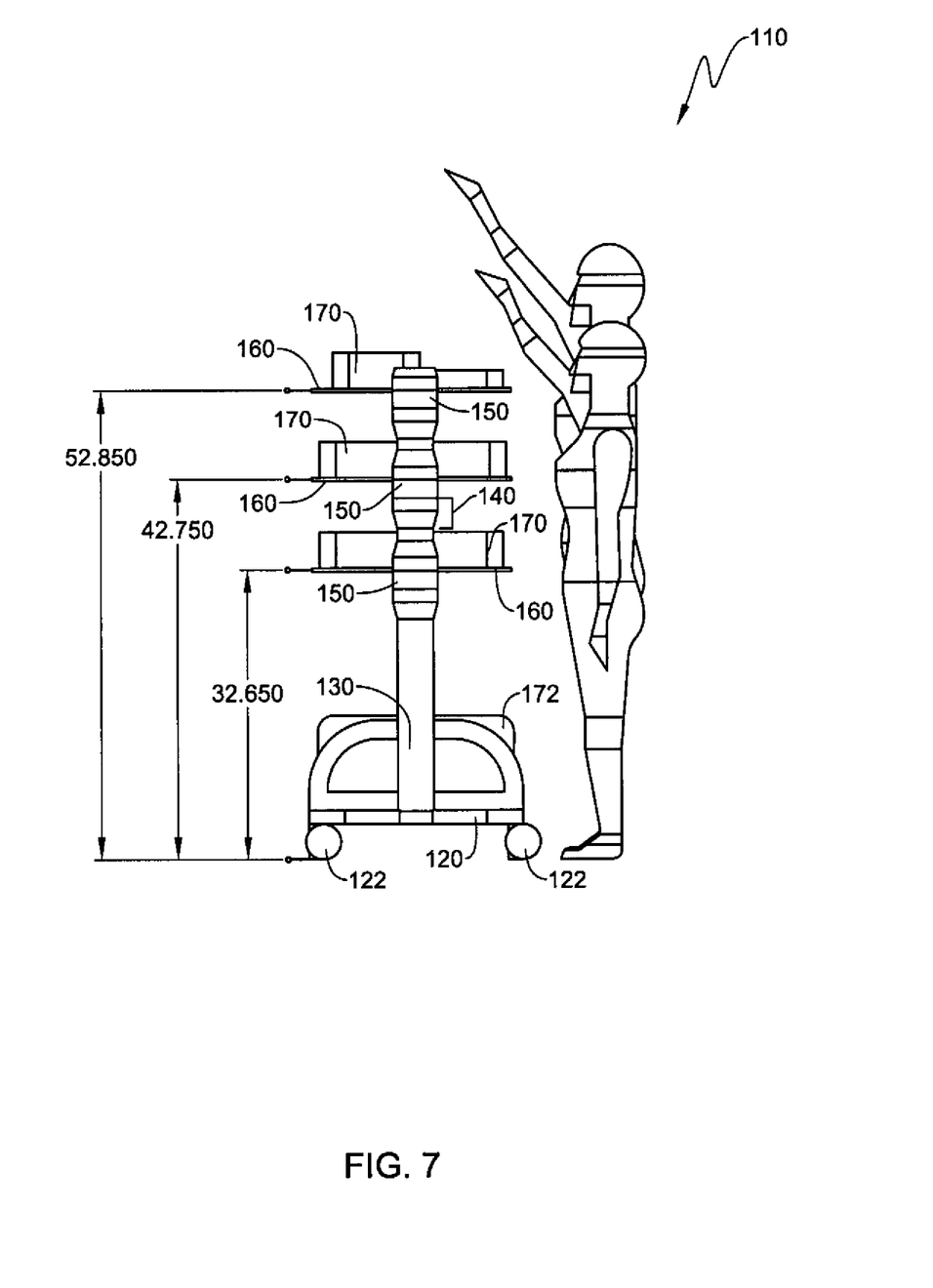
FIG. 7 is a side view illustration of a modular medical instrument table, in accordance with the second exemplary embodiment of the present disclosure.

FIG. 7 is a side view illustration of a modular medical instrument table 110, in accordance with the first exemplary embodiment of the present disclosure. The size and dimensions of the table 110 and the various components within the table 110 may vary, depending on design. The overall height of the table 110 may be designed for comfort and convenience to a user, and may include any size. For example, as is illustrated in FIG. 7, the height of the uppermost shelf 160 may be approximately 52 inches, whereas the lowermost shelf 160 may be approximately 32 inches. Generally, a working area from the shoulder to waist of an average sized human being may be desirable. In FIG. 7, the height of the models depicted are for a larger model and a smaller model, with approximately 10 inches between each of the shelves 160. Any height of the table 110 is available, and the height of the shelves 160 may be adjustable depending on who is using the table 110. It is noted that the configurations depicted in FIGS. 1-7 are not necessarily to scale, and are not considered limiting to the scope of the present disclosure.

When the arms 150 are positioned substantially above the base 120, as is shown in FIGS. 4-7, the table 110 may have a footprint that minimizes the amount of space it takes up in an operating room and/or storage facility. For example, the footprint may be 24 inches by 63 inches, although any size footprint is considered within the scope of the present disclosure. The dimensions of the shelves 160 may be 21 inches by 21 inches, for example, although smaller and larger shelves 160 may be used as well. Dimensions of the other components, including the extenders 140, arms 150 and medical instrument sterilization containers 170 may also vary by design.

Additionally, any number of components may be used with the table 110. For example, three levels of shelves 160 may be used, as is shown in FIGS. 4-7, but one, two, or four or more levels of shelves 160 may also be used. The levels of shelves 160 may be spaced any distance apart, such as 10 inches, 15 inches, etc. The table 110 may also include other features to enhance usability, efficiency and convenience of use. These features may include labeling systems, identification systems or other systems that help organize medical procedures, medical instruments or another aspect within the medical field.

Figure 8:
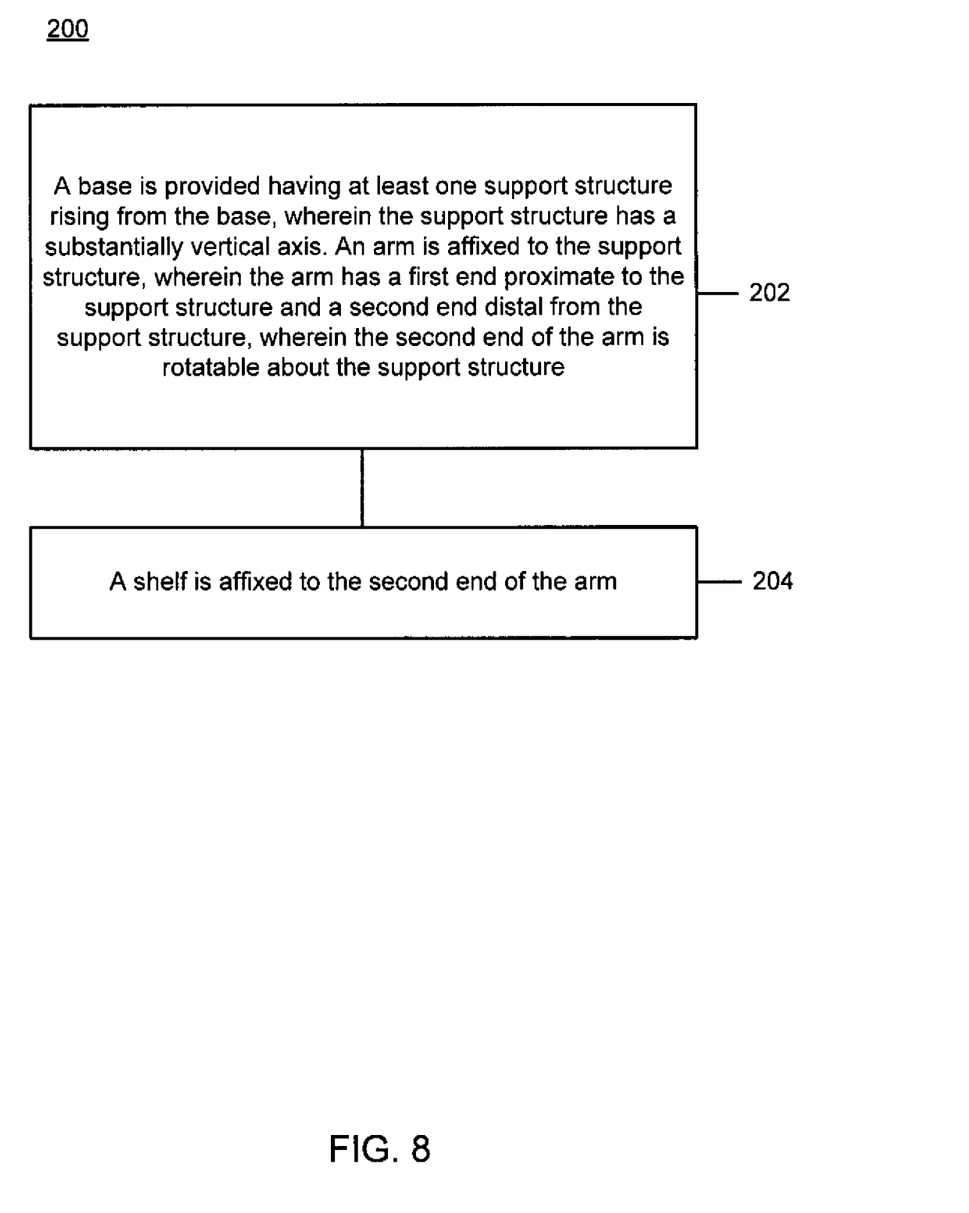
FIG. 8 is a flowchart illustrating a method of method of assembling a modular medical instrument table, in accordance with the first exemplary embodiment of the disclosure.

FIG. 8 is a flowchart 200 illustrating a method of method of assembling a modular medical instrument table 10, in accordance with the first exemplary embodiment of the disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 202, a base is provided having at least one support structure rising from the base, wherein the support structure has a substantially vertical axis. An arm is affixed to the support structure, wherein the arm has a first end proximate to the support structure and a second end distal from the support structure, wherein the second end of the arm is rotatable about the support structure (Block 202). A shelf is affixed to the second end of the arm (Block 204).

Any additional number of steps or processes may be included. For example, an extender may be placed proximate to the arm, wherein the extender is in axial alignment with the support structure. A second arm may then be affixed to the support structure, wherein the second arm has a first end proximate to the support structure and a second end distal from the support structure, wherein the second end of the second arm is rotatable about the support structure, and wherein the extender is positioned between the arm and the second arm. If a top cap or end cap is used, it may be placed on the uppermost surface of the support structure. After a shelf is properly installed, a medical instrument container, such as one used during a medical instrument sterilization processes may be placed on the shelf. When a medical professional desires to gain access to an instrument within the container, the cover of the container may be removed and placed on a rack. The rack may be positioned on the base and may be sized to hold at least one medical instrument container cover.

Figure 9:
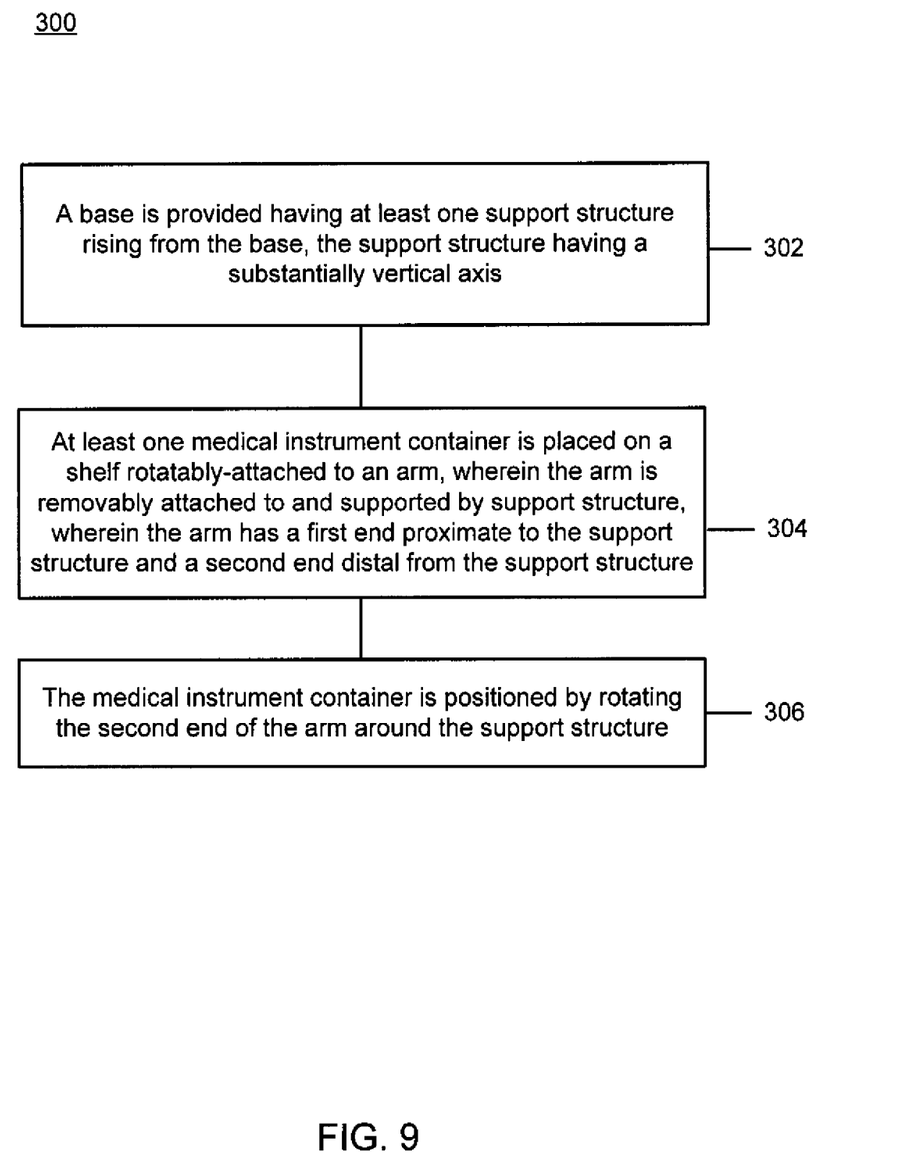
FIG. 9 is a flowchart illustrating a method of method of using a modular medical instrument table, in accordance with the first exemplary embodiment of the disclosure.

FIG. 9 is a flowchart 300 illustrating a method of method of using a modular medical instrument table 10, in accordance with the first exemplary embodiment of the disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 302, a base is provided having at least one support structure rising from the base, the support structure having a substantially vertical axis. At least one medical instrument container is placed on a shelf rotatably-attached to an arm, wherein the arm is removably attached to and supported by support structure, wherein the arm has a first end proximate to the support structure and a second end distal from the support structure (Block 304). The medical instrument container is positioned by rotating the second end of the arm around the support structure (Block 306).

The method may include any number of additional steps. For example, a cover may be removed from the medical instrument container and the cover may be on a rack positioned on the base, wherein the rack is sized to hold the cover. A second medical instrument container may be placed on a second shelf rotatably-attached to a second arm, wherein the second arm is removably attached to and supported by support structure, wherein the second arm has a first end proximate to the support structure and a second end distal from the support structure. An extender may be positioned between the arm and the second arm, wherein the extender is in axial alignment with the support structure, and wherein the extender positions the second arm a predetermined distance from the arm. Depending on the desired distance between shelves, a plurality of extenders may be connected together. The extenders may be positioned between the arm and the second arm, wherein the plurality of extenders are in axial alignment with the support structure, and wherein the plurality of extenders position the second arm a predetermined distance from the arm.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A modular medical instrument table comprising:
a base;
a support structure rising from the base and terminating at an upper edge, the support structure having a substantially vertical axis;
at least two substantially cylindrical arm attachment structures connected to the support structure, the at least two arm attachment structures each comprising:
a bottom portion;
a top portion;
an uninterrupted planar portion between the top portion and the bottom portion;
a non-threaded, friction fit female connector located within the bottom portion; and
a non-threaded, friction fit male connector formed on the top portion, wherein the non-threaded, friction fit male connector of a first of the at least two arm attachment structures is engaged with the non-threaded, friction fit female connector of a second of the at least two arm attachment structures, wherein the first arm attachment structure is secured to the second arm attachment structure with the engagement between the non-threaded, friction fit male connector and the non-threaded, friction fit female connector, wherein the at least two arm attachment structures are each substantially aligned with the substantially vertical axis of the support structure;
at least a first arm removably affixed to an exterior surface of the first attachment structure, the first arm having a first end proximate to the substantially vertical axis of the support structure and a second end distal from the substantially vertical axis of the support structure, wherein the second end of the arm is rotatable about the substantially vertical axis of the support structure; and a shelf attached to the second end of the arm.

2. The modular medical instrument table of claim 1, further comprising a top cap axially aligned with the substantially vertical axis of the support structure and positioned above an upper-most surface of an upper-most arm attachment structure of the at least two arm attachment structures.

3. The modular medical instrument table of claim 1, further comprising a medical instrument container positioned on the shelf.

4. The modular medical instrument table of claim 1, further comprising a plurality of legs supporting the base.

5. The modular medical instrument table of claim 4, wherein the plurality of legs further comprising rolling casters.

6. The modular medical instrument table of claim 1, further comprising a rack positioned on the base, wherein the rack is sized to hold at least one medical instrument container cover.

7. The modular medical instrument table of claim 6, wherein the rack further comprises a plurality of substantially vertically-oriented dividing structures positioned substantially parallel to each other.

8. The modular medical instrument table of claim 7, wherein a height of each of the plurality of substantially vertically-oriented dividing structures exceeds a distance between two abutting substantially vertically-oriented dividing structures.

9. The modular medical instrument table of claim 1, wherein the shelf is attached to the second end of the arm with a rotatable attachment, wherein the rotatable attachment allows the shelf to rotate.

10. The modular medical instrument table of claim 1, wherein the shelf attached to the second end of the arm is movable between at least a first and a second position, wherein the shelf is located directly above the base in the first position and wherein the shelf is not located directly above the base in the second position.

11. The modular medical instrument table of claim 10, wherein the shelf fits entirely within a footprint of the base when the shelf is located in the first position.

12. The modular medical instrument table of claim 1, wherein the at least one arm further comprises at least three arms, each of the at least three arms removably affixed to one of the at least two arm attachment structures and positioned vertical to each other, wherein each of the at least three arms is positioned entirely above the upper edge of the at least one support structure, and wherein each of the at least three arms is positioned in a different radial position about the at least one support structure.

13. The modular medical instrument table of claim 1, wherein the first end of the first arm further comprises two independent members connected to a cylindrical mount, wherein the two independent members are connected on opposing sides of the cylindrical mount, and wherein the two independent members converge at a position between the first end and the second end of the first arm.

14. The modular medical instrument table of claim 13, wherein the cylindrical mount is removably positioned over the first arm attachment structure.

15. The modular medical instrument table of claim 1, wherein the non-threaded, friction fit male connector of the first of the at least two arm attachment structures is engaged with the non-threaded, friction fit female connector of a second of the at least two arm attachment structures by a snap connection, wherein the snap connection further comprises the non-threaded friction fit male connector snapped within the non-threaded, friction fit female connector.

16. The modular medical instrument table of claim 1, wherein the non-threaded friction fit male connector further comprises a substantially cylindrical post rising from the top portion, wherein an upper edge of the non-threaded, friction fit male connector extends radially outwards beyond an external surface of the substantially cylindrical post.

17. The modular medical instrument table of claim 16, wherein the upper edge further comprises an entire upper radial edge of the substantially cylindrical post.

18. The modular medical instrument table of claim 1, wherein at least one of the at least two arm support structures is hollow.

19. A modular post system for supporting a table arm used with a modular medical instrument table, the modular post system comprising:

at least two substantially cylindrical arm attachment structures, the at least two arm attachment structures each comprising:

a bottom portion;

a top portion;

an uninterrupted planar portion between the top portion and the bottom portion;

a non-threaded, friction fit female connector located within the bottom portion; and a non-threaded, friction fit male connector formed on the top portion, wherein the non-threaded, friction fit male connector of a first of the at least two arm attachment structures is engaged with the non-threaded, friction fit female connector of a second of the at least two arm attachment structures, wherein the first arm attachment structure is secured to the second arm attachment structure with the engagement between the non-threaded, friction fit male connector and the non-threaded, friction fit female connector, wherein the at least two arm attachment structures are positioned substantially aligned.

\* \* \* \* \*